United States Patent [19]

Bertolacini et al.

[11] 4,330,435

[45] May 18, 1982

[54] CATALYST FOR THE DISPROPORTIONATION OF PETROLEUM HYDROCARBONS

[75] Inventors: Ralph J. Bertolacini, Chesterton, Ind.; Dae K. Kim, Naperville, Ill.; Gerald M. Lehmann, Gary, Ind.

[73] Assignee: Standard Oil Company (Indiana), Chicago, Ill.

[21] Appl. No.: 1,952

[22] Filed: Jan. 8, 1979

Related U.S. Application Data

[62] Division of Ser. No. 849,605, Nov. 8, 1977, Pat. No. 4,167,530.

[51] Int. Cl.$^3$ .............................................. B01J 29/26
[52] U.S. Cl. ............................................... 252/455 Z
[58] Field of Search ..................... 252/455 Z; 585/475

[56] References Cited

U.S. PATENT DOCUMENTS

| | | | |
|---|---|---|---|
| 2,964,463 | 12/1960 | Miller et al. | 252/455 R |
| 3,281,483 | 10/1966 | Benesi et al. | 585/475 X |
| 3,392,108 | 7/1968 | Mason et al. | 252/455 Z |
| 3,546,102 | 12/1970 | Bertolacini | 252/455 Z |
| 3,562,345 | 2/1971 | Mitsche | 585/475 |
| 3,699,181 | 10/1972 | Knecak et al. | 585/475 |
| 3,729,521 | 4/1973 | Gutberlet et al. | 585/475 |
| 3,798,154 | 3/1974 | Bertolacini et al. | 252/455 Z |

*Primary Examiner*—Carl F. Dees
*Attorney, Agent, or Firm*—William C. Clarke; William T. McClain; William H. Magidson

[57] ABSTRACT

Process for disproportionation of petroleum hydrocarbons which comprises contacting in a reaction zone said petroleum hydrocarbon under suitable disproportionation conditions with a catalytic composition comprising a tungsten/molybdenum component, said tungsten/molybdenum component deposited upon an acidic cracking component comprising a mordenite large pore crystalline aluminosilicate material and a refractory inorganic oxide.

7 Claims, 2 Drawing Figures

FIG. 1

CATALYST FOR THE DISPROPORTIONATION OF PETROLEUM HYDROCARBONS

This is a division of application Ser. No. 849,605, filed Nov. 8, 1977, now U.S. Pat. No. 4,167,530.

BACKGROUND OF THE INVENTION

The present invention is directed to a process for the conversion of petroleum hydrocarbons. More particularly it is directed to a process for the disproportionation of petroleum hydrocarbons. Still more particularly, it is directed to a vapor-phase process for the disproportionation of alkyl aromatic hydrocarbons.

The invention pertains to a process for treating mineral oils which results in a chemical alteration of at least some of the hydrocarbon molecules of the mineral oils to form mineral oils having different properties and different chemical structures. These different chemical compounds result from the intramolecular migration of alkyl groups. For example in the disproportionation of toluene, there results benzene and the various xylenes.

DESCRIPTION OF THE PRIOR ART

The process of disproportionation or transalkylation of petroleum hydrocarbons in the prior art is taught as requiring less severe conditions than other hydrocarbon conversion process such as hydrogenation and hydrocracking (destructive hydrogenation). Generally, the disproportionation of petroleum hydrocarbons causes side reactions to occur with the formation of lower hydrocarbons and the deposition of carbon materials. Accordingly, in the present state of the art, there is a need for more active disproportionation catalysts which have greater selectivity to the desired transalkylated aromatic hydrocarbon and are more stable to process conditions such as hydrocarbon sulfur content and operating temperatures. A particular need exists for improvement of selectivity with lower operating severity to reduce deposition of carbon materials and undesired hydrocracking.

In the case of aromatic hydrocarbons, rearrangement of alkyl groups in the presence of Friedel-Crafts catalysts is well-known. Such rearrangements as the transfer of alkyl groups from toluene to form benzene and xylenes and the transfer of alkyl groups from xylenes to form toluene and trimethylbenzenes are catalyzed by strongly acidic catalysts. The role of the catalyst and the reaction mechanism in the disproportionation of alkyl benzenes have been the subjects of much speculation.

The related reaction of isomerization has indicated that the acidity and amount of catalyst affect the course of the reaction. Although disproportionation requires more rigorous conditions than isomerization, it has been postulated that the rate of disproportionation in the case of a hydrogen fluoride-boron trifluoride catalyst is directly related to the amount of hydrocarbon dissolved in the catalyst phase and the temperature of the reaction (A. P. Lien et al, IEC, 75, 2409) It has been further postulated (D. A. McCauley et al, IEC, 75 2413) that the mechanism of alkyl group transfer in disproportionation reactions depends upon the severity of the reaction conditions. Under moderate conditions, simple alkyl disproportionation is a bimolecular reaction between an aromatic cation and a neutral aromatic molecule. Under severe conditions, the aromatic cation dissociates unimolecularly into a neutral aromatic molecule and an alkyl carbonium ion. The carbonium ion then reacts further by isomerization, alkylation, polymerization and hydride-ion abstraction. Disproportionation by the unimolecular mechanism under severe conditions is accompanied by a considerable amount of side reaction and may lead to a complex product. The advantages of a reaction under moderate conditions are consequently important economically. Catalysis Vol. IV, P. H. Emmett, editor, Reinhold Publishing Corp. 1958, p. 498–499.

A new vapor-phase disproportionation process has been found. The catalysts employed in the process are very active catalytic compositions. It is believed that these catalysts are not only superior catalysts for disproportionation, but also are suitable catalysts for hydrocracking.

In the prior art, many catalyst compositions useful in hydrogenation and disproportionation processes are to be found. The catalyst compositions taught are specific and particular. Nozaki, U.S. Pat. No. 2,744,052, which is incorporated by reference, discloses a catalyst of tungsten-molybdenum and nickel impregnating an alumina carrier for use in hydrogenating hydrocarbon oils. The unexpected superiority of the nickel-molybdenum-tungsten-alumina catalyst is said to be caused by the interaction of all the components in specified mole ratios to produce an enhanced activity and are equally important. Miller et al, U.S. Pat. No. 2,964,463, teaches a catalyst composition for a hydrogenation process which shows that a particular combination of promoters comprising molybdenum oxide and tungsten on a silica-alumina support in certain weight proportions is unexpectedly superior. Benesi et al., U.S. Pat. No. 3,281,483, teaches that the hydrogen form of mordenite is an excellent catalyst for the disproportionation of alkylaromatics such as toluene. Other acidic solids such as silica-alumina cracking catalyst and platinum on halogenated alumina reforming catalyst are taught as having little or no activity for the disproportionation of alkylaromatics under similar conditions. Benesi teaches that a particular catalytic metal or promoter which enhances catalytic activity and stability can be incorporated into the mordenite. Benesi indicates the particular metal can be of Group 1b or Group VIb or the iron group of Group VIII. Benesi does not teach the synergistic combination of metals with mordenite. Mitsche et al, U.S. Pat. No. 3,562,345 teaches a disproportionation catalyst of a crystalline aluminosilicate containing alumina fixed in combination which can be as a component of a catalyst comprising one or more metals of Groups VIb and VIII to effect a composite catalyst for a variety of hydrocarbon conversion reactions such as hydrocracking. Mitsche, U.S. Pat. No. 3,644,219, teaches a method of preparing a crystalline aluminosilicate containing alumina which entails aging in an alkaline media. Mitsche et al, U.S. Pat. No. 3,677,973 also teaches an aging process for the preparation of a mordenite catalyst as does Mitsche et al, U.S. Pat. No. 3,720,726. Kovach et al, U.S. Pat. No. 3,597,491, teaches an alkyl transfer of alkylaromatics using a catalyst comprising a Group VIb metal deposited on a Type Y zeolite base. Kmecal, U.S. Pat. No. 3,699,181, teaches a process for alkyl transfer with a catalyst comprising a Group VIb metal on a synthetic mordenite base. Promoters selected from Group I, Group II, Group IV and the Rare Earth metals can be added to the catalyst. Combinations of a mordenite, zinc and another metal are taught in U.S. Pat. No. 3,819,736, Sato et al. In no case in the prior art is there taught the combination of the oxide of molybdenum, the oxide of tungsten, the co-catalytic support of H-mordenite and the porous refractory inorganic oxide of alumina.

SUMMARY OF THE INVENTION

Broadly, in accordance with the present invention, there is provided a process for the disproportionation of a petroleum hydrocarbon fraction, which process comprises contacting in a reaction zone a petroleum hydrocarbon fraction with a catalytic composition under suitable disproportionation conditions. Said catalytic composition comprises two members selected from the group consisting of the oxides of metals of Group VIb of the Periodic Table of the Elements and mixtures thereof deposited upon a solid acidic cracking support. This acidic co-catalytic solid support comprises a mordenite type aluminosilicate material and a porous refractory inorganic oxide. The preferred metals of Group VIb are molybdenum and tungsten. Preferably the mordenite is suspended in and distributed throughout a matrix of the refractory inorganic oxide. The preferred refractory inorganic oxide is a catalytically active alumina.

Preferably, the mordenite-type aluminosilicate material has been cation-exchanged with a member selected from the group consisting of an alkaline earth metal, a rare earth metal, hydrogen, and a hydrogen precursor to reduce the sodium content to a level that is less than 1 weight percent, calculated as the metal. The mordenite-type aluminosilicate material can be present in the co-catalytic solid support in an amount within the range of about 5 weight percent to about 95 weight percent, based on the weight of said support. The porous refractory inorganic oxide can be present in the co-catalytic solid support in an amount within the range of about 95 weight percent to about 5 weight percent, based on the weight of the solid support. The preferred metals of the Group VIb can be present in an amount within the range of about 2 weight percent to about 20 weight percent, based on the combined weights of the co-catalytic solid support and the oxides of the metals in the catalytic composition.

The catalysts of this invention are very active. Therefore, the catalysts are subjected to a treatment with a sulfur-providing compound to inhibit the demethanation reaction which normally occurs over such catalyst when the metals of the catalyst are primarily in the reduced state. Such sulfur-providing compounds such as hydrogen sulfide and carbon disulfide can be employed.

An embodiment of the process of this invention is a process to convert a petroleum hydrocarbon stream comprising single-ring aromatic hydrocarbons wherein alkyl groups are transferred from one molecule to another. This latter process comprises contacting the petroleum stream in a hydrocarbon-conversion zone with a catalytic composition of this invention in the presence of a hydrogen-affording gas under suitable disproportionation conditions.

Accordingly, a specific embodiment of the process of this invention is a process for the disproportionation of a petroleum hydrocarbon fraction comprising toluene. The process of this specific embodiment comprises contacting the petroleum hydrocarbon fraction with a catalytic composition of this invention in the presence of a hydrogen-affording gas under disproportionation conditions comprising an average temperature between about 600° F. and about 1100° F., a pressure of about 100 to about 1,000 psig, a weight hourly space velocity (WHSV) of about 1.0 to about 20 weights of hydrocarbon per hour per weight of catalyst, and a hydrogen-to-hydrocarbon ratio of about 1,000 standard cubic feet of hydrogen per barrel of hydrocarbon (SCFB) to about 50,000 SCFB, and recovering the disproportionated product and separating it into its various component hydrocarbons. The catalyst of this specific embodiment of the instant invention comprises tungsten and molybdenum, their oxides, sulfides, and/or mixtures thereof on a solid acidic cracking component comprising 5 to 95 weight percent mordenite large-pore crystalline aluminosilicate material suspended in and distributed uniformly throughout a matrix of catalytically active alumina. The catalyst is pretreated with gas containing a minor amount of hydrogen sulfide, e.g., about 8 percent hydrogen sulfide. The pretreatment is carried out at a pressure of about 300 psig for 2 hours. The flow rate of the pretreating gas is maintained between about 50,000 and about 300,000 standard cubic feet per hour per ton of catalyst. The temperature of the catalyst is initially about 500° F. and is raised to a temperature of about 750° F. during the first hour and then maintained at the latter temperature during the second hour of the pretreatment.

DESCRIPTION AND PREFERRED EMBODIMENTS OF THE INVENTION

The process of this invention will be understood from the following description and examples.

The process of this invention is a process for the disproportionation of petroleum hydrocarbons. Particularly, it is a process for the disproportionation of alkyl aromatic hydrocarbons wherein the alkyl groups are transferred from one molecule to another.

The success of this disproportionation process is due primarily to the use of particular catalytic compositions which are employed therein and the operating conditions that are used.

Typical feedstocks of the present invention are petroleum hydrocarbon streams which contain single-ring aromatic hydrocarbons which boil below about 650° F. Such aromatic hydrocarbon streams may be a petroleum hydrocarbon fraction which contains aromatics or it may be a purified aromatic hydrocarbon. For example, the feedstock of this invention may contain toluene, ortho-xylene, meta-xylene, and para-xylene, trimethylbenzenes, and tetramethylbenzenes.

Typically the feedstock is mixed with a hydrogen-affording gas and preheated to a suitable disproportionation temperature, and then transferred to the disproportionation reaction zone, which may contain one or more reactors. Advantageously, the feed is substantially completely vaporized before being introduced into the reaction zone.

The feedstock is contacted in the disproportionation reaction zone with the hereinafter described catalyst in the presence of hydrogen-affording gas. Advantageously, a hydrogen-to-hydrocarbon ratio of at least 1,000 SCFB is employed, and the hydrogen-to-hydrocarbon ratio may range up to 50,000 SCFB. Preferably, the hydrogen-to-hydrocarbon ratio may range between about 5,000 SCFB and 30,000 SCFB. Other operating conditions comprise an elevated temperature of about 600° F. to about 1100° F., preferably about 750° F. to about 1000° F.; an elevated pressure of about 100 psig to about 1,000 psig, preferably about 150 psig to about 500 psig; and WHSV of about 0.1 to about 20 weights of hydrocarbon per hour per weight of catalyst, preferably about 1 to about 10 weights of hydrocarbon per hour per weight of catalyst.

The exothermic demethanation reaction that occurs in the disproportionation reaction zone may be controlled by the treatment of the catalyst with sulfur compounds, such as hydrogen sulfide and carbon disulfide, either prior to or at the start of the disproportionation reaction. If hydrogen sulfide is used, the catalyst is advantageously subjected to the hydrogen sulfide prior to its use as a catalyst for disproportionation. If carbon disulfide is employed, it may be added to the hydrocarbon feed during the initial stages of the run. The treatment must be of such duration and the amount of sulfur-providing compound must be such that substantial amounts of the metals of the catalyst are converted to their sulfides. It is not known at this time what comprises substantial amounts of the metals. However, if the metals are in the reduced state, they will more actively catalyze the demethanation reaction. Therefore, the greater the percentage of the metal in the sulfide form, the better is the inhibition of the demethanation. Typically, approximately 0.15 lb. of sulfur is used per pound of catalyst.

The catalytic composition of the process of this invention comprises a hydrogenation component disposed upon a solid acidic cracking support. The hydrogenation component comprises two members selected from the group consisting of the oxides of metals of Group VIb of the Periodic Table of Elements and mixtures thereof. The pertinent Periodic Table of Elements may be found on the inside of the back cover of HANDBOOK OF CHEMISTRY AND PHYSICS, 45th edition, Robert C. Weast, editor, Chemical Rubber Company, Cleveland, Ohio (1964). The preferred Group VIb metals are tungsten and molybdenum. Molybdenum is present in an amount within the range of about 1.0 to about 20 weight percent, expressed as $MoO_3$ and based upon the weight of the catalytic composition, while tungsten is present in an amount within the range of about 1 to about 10 weight percent, expressed as $WO_3$ and based upon the weight of the catalytic composition.

The solid acidic cracking support of the catalyst employed in the process of the present invention comprises a mordenite-type, large-pore crystalline aluminosilicate material and a suitable refractory inorganic oxide. Preferably, the mordenite-type, large-pore crystalline aluminosilicate material is suspended in and distributed throughout the matrix of the refractory inorganic oxide. The mordenite-type, large-pore crystalline aluminosilicate material is present in an amount within the range of about 5 to about 95 weight percent, based upon the weight of the support.

The refractory inorganic oxide component of the support of the catalyst that is employed in the process of the present invention may be an oxide of a single metal, or it may be a mixture of the oxides of two or more metals of Groups III and IV of the Periodic Table of Elements. For example, the refractory inorganic oxide component may be catalytically active alumina, or it may be a mixture of silica and alumina, or it may be a mixture of boria, titania, and alumina. The preferred refractory inorganic oxide is a catalytically active alumina.

An example of the refractory inorganic oxide component that is employed in the catalyst of this invention is PHF or Aero-1000 Alumina manufactured by American Cyanamid Corp. It is described as a high-purity γ-alumina, the inspection data being: surface area 206 $m^2/g$, pore volume 0.6 cc/g, average pore diameter 90 Å (Angstroms), sodium content 0.1 wgt. %, silicon content 0.02 wgt. %, iron content 0.025 wgt %.

The aluminosilicate material that is a component of the support of the catalytic composition that is employed in the process of the present invention is a mordenite-type, large-pore crystalline aluminosilicate material. It is sometimes hereinafter referred to as "mordenite aluminosilicate material". By large pore material is meant a material that has pores which are sufficiently large to permit the passage thereinto of benzene molecules and larger molecules, and the passage therefrom of reaction products. For use in catalysts that are employed in petroleum hydrocarbon conversion processes, it is preferred to employ a large-pore crystalline aluminosilicate material having a pore size of at least 6 to 10 Angstrom units (Å). The mordenite aluminosilicate material of the catalyst of the present invention possesses such a pore size.

A preferred mordenite-type aluminosilicate material is the synthetic Zeolon manufactured by the Norton Chemical Company. Zeolon-H is the hydrogen form of this synthetic mordenite. Mordenite is characterized by its high silica-to-alumina ratio and its crystal structure. The mordenite may have a silica-to-alumina ratio within the range of about 6 to about 100. The composition of mordenite is given in Kirk-Othmer, "Encyclopedia of Chemical Technology", first edition, Volume 12, page 297 (1954), as $(Ca, Na_2)Al_2Si_9O_{22}.6H_2O$. The proposed structure is one in which the basic building block is a tetrahedron consisting of 1 silicon or aluminum atom surrounded by four oxygen atoms. The crystal structure is made up of 4- or 5-membered rings of these tetrahedra. These 4- and 5-membered rings are believed to give the structure its stability. The chains are linked together to form a network having a system of large parallel channels interconnected by small cross channels. Rings of 12 tetrahedra form the large channels. Other synthetic zeolites also have such 12-membered rings, but they have interconnected cages, whereas the mordenite has parallel channels of uniform diameter. For example, synthetic faujasite, which has the formula $Na_3Al_3Si_4O_{14}$, is characterized by a 3-dimensional array of pores which consist of 12–13 Angstrom (Å) cages interconnected through 8–9 Å windows.

The mordenite aluminosilicate material that is preferred, the Zeolon manufactured by the Norton Chemical Company, with its high ratio of silica to alumina exhibits the ability to undergo complete acid exchange from the original sodium form to the hydrogen form.

The theoretical silica-to-alumina ratio is about 10 to 1 and the effective pore diameter in Angstroms (Å) is within the range of 6 to 9 Å. The surface area in square meters/gram is within the range of 400–450 m$^2$/g and its static water capacity in weight percent is within the range of 10–11%.

The mordenite in the catalytic composition of the present invention may be in the unexchanged cation form containing exchangeable sodium and/or calcium ions, or other alkali metal or alkaline earth metal ions. Preferably, the alkali metal cations, such as sodium ions, may be replaced or cation-exchanged with a member selected from the group consisting of an alkaline earth metal, a rare earth metal, hydrogen, and a hydrogen precursor to provide an alkali metal content in the mordenite that is less than 1 weight percent, calculated as the metal. Ammonium ions comprise a hydrogen precursor and may be employed to cation-exchange the alkali metal of the mordenite. Heat is employed to drive off ammonia leaving the mordenite in the hydrogen form. Mordenite differs from other aluminosilicates in that substantially all the exchangeable metal cations may be replaced with hydrogen ions without causing destruction of the characteristic crystal structure of the mordenite.

The porous refractory inorganic oxide that is employed in the catalytic composition of the present invention may be a catalytically active alumina, silica-alumina, silica-magnesia, titania-alumina, zinc-oxide-alumina, and the like. Catalytically active alumina, such as gamma-alumina and eta-alumina, is the preferred refractory inorganic oxide. Such alumina should have a pore diameter of about 70 Angstroms to about 200 Angstroms and a surface area of at least 100 square meters per gram. Suitably, the surface area should be within the range of about 200 square meters per gram to about 500 square meters per gram.

The co-catalytic composition of the present invention may be prepared in various ways. For example, finely divided mordenite-type aluminosilicate material may be stirred into a sol or gel of the refractory inorganic oxide and soluble compounds of the Group VIb metals added to the sol or gel, followed by the cogelling of the sol or gel mixture by the addition of dilute ammonia. The resulting cogelled material is then dried and calcined. In another method of preparation, the finely divided mordenite is mixed into a sol or gel of the refractory inorganic oxide, the sol or gel mixture is cogelled by the addition of dilute ammonia and the resulting gel is subsequently dried, pelleted, calcined, cooled, and impregnated with a solution or solutions of the Group VIb metals. As an alternate method of preparation, a hydrogel of the refractory inorganic oxide is blended with finely divided aluminosilicate material, and a solution or solutions of soluble compounds of the Group VIb metals are added to this blend, and the resulting mixture is thoroughly blended. The blended mixture is then dried, pelleted, and calcined. Suitable drying conditions for use in the above described metal manufacturing methods comprise a temperature in the range of about 200° F. to about 400° F. and a drying time of about 5 to 30 hours. Suitable calcination conditions comprise a temperature in the range of about 900° to 1,400° F. and a calcination time of about 2 to about 20 hours. Preferred drying and calcination conditions are a temperature of about 250° F. for about 16 hours and a temperature of about 1,000° F. for about 6 hours, respectively.

The catalytic composition that is employed in the process of the present invention can be prepared in several other ways. For example, the mordenite-type, large-pore crystalline aluminosilicate material can be pulverized into a finely-divided state and then physically admixed with a finely-divided powder of the selected refractory inorganic oxide component. Ater a thorough blending of the two solid components, the resulting mixture may be co-pelleted, and impregnated with one or more solutions of the metals of the hydrogenation component, i.e., the metals of Group VIb. The resulting composition is thoroughly mixed to form a blended composition, which is subsequently dried to a moisture content ranging from about 20 to 40 weight percent, based upon the total weight of the composition. The dried material is then calcined at a temperature within the range of about 900° to about 1100° F.

The following is another method of preparation. The mordenite-type, large-pore crystalline aluminosilicate material in a finely-divided state may be added to a hydrosol or a hydrogel of the refractory inorganic oxide component and blended therein to form a homogenous mixture. The hydrogenation component, i.e., the metals of Group VIb, are added in the form of heat-decomposable components to this homogenous mixture. These heat-decomposable components may be added in a single solution or in several solutions. The resulting composition is then thoroughly mixed, dried, and calcined, as described above.

Alternatively, the homogenous mixture of the above paragraph may be dried and pelleted, or dried, and the resulting material may be impregnated with the hydrogenation component, followed by drying and calcining, as described above.

The invention comprises a process for the disproportionation of alkylaromatics which process consists essentially of contacting an alkylaromatic stream in a reaction zone under disproportionation conditions and in the presence of a catalyst to furnish a product containing transalkylated aromatics, said catalyst comprising a hydrogenation component which comprises two Group VIb metals deposed upon a solid support of a co-catalytic component comprising H-mordenite and a porous refractory inorganic oxide, said refractory inorganic oxide being selected from the group consisting of catalytically active alumina or silica-alumina, silica, zirconia, titania and mixtures thereof, and said Group VIb metals being present as members selected from the group consisting of (1) the elements, (2) their oxides, (3) their sulfides, and (4) mixtures thereof. When the refractory inorganic oxide is alumina, the catalyst co-support contains at least 5 weight % alumina, preferably 80 weight % alumina.

Embodiments of the process of the present invention may be found in the following examples. These embodiments and examples are presented for purposes of illustration only and are not intended to limit the scope of the invention.

EXAMPLE I

Figure 1:
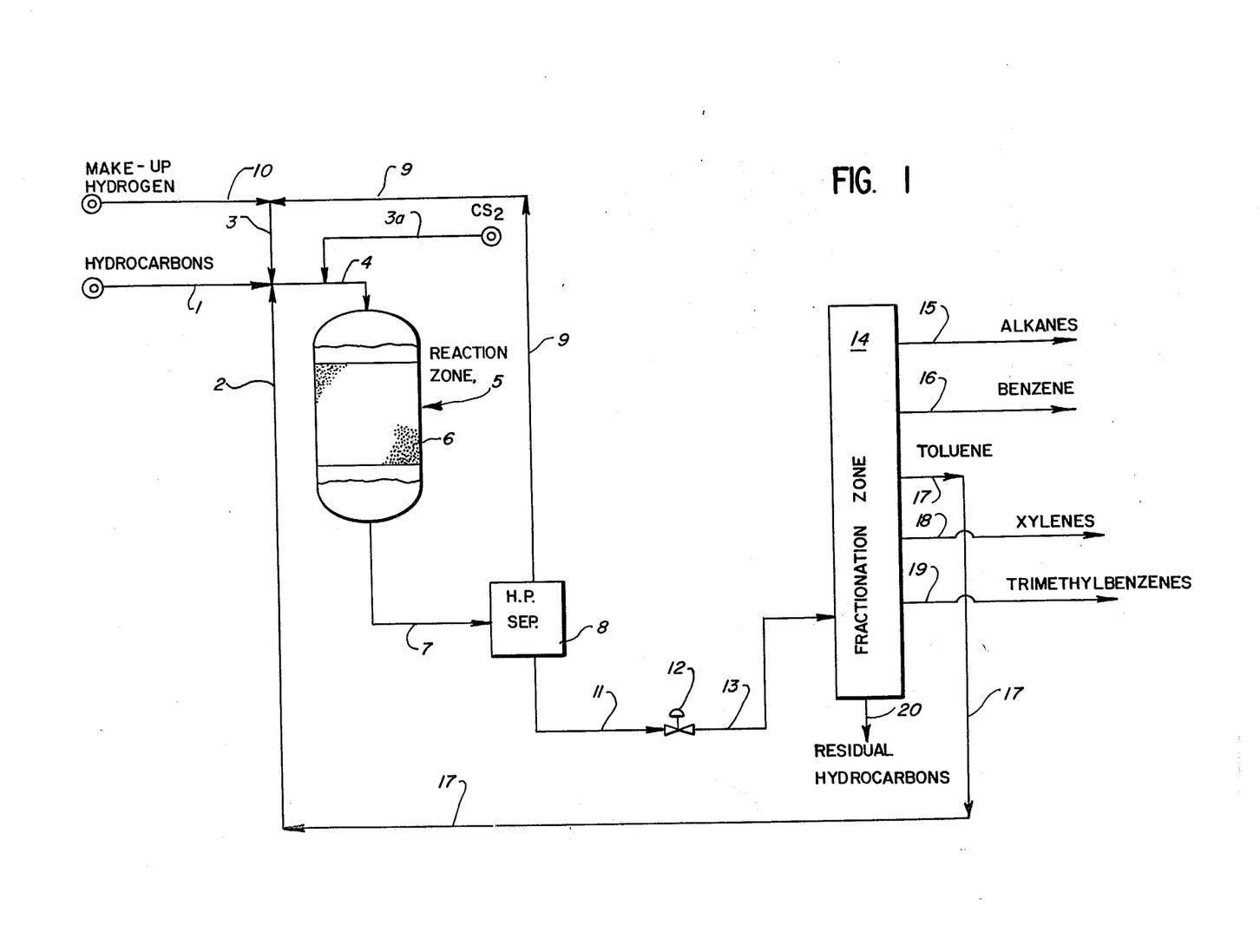
FIG. 1 is a simplified process flow scheme of a specific embodiment of the process of the present invention.

A specific embodiment of the process of the present invention is presented in this example. A simplified process flow scheme for this embodiment is depicted in FIG. 1. Auxiliary equipment, such as pumps and heat exchangers, is not shown in the drawing. Such auxiliary equipment is well-known to those skilled in the art and the uses and locations of this equipment in this particular process system will be recognized easily by those having ordinary skill in the art.

Fresh feedstock comprising toluene is introduced into the process system by way of line 1. Recycle hydrocarbons from line 2 are mixed with the fresh feedstock in line 1. Hydrogen-containing gas is introduced into the hydrocarbon stream by way of line 3, carbon disulfide is added by way of line 3a, and the resulting mixture is passed through line 4 and heat-exchange equipment (not shown) into reaction zone 5. Reaction zone 5 contains a catalyst bed or catalyst beds 6. The catalyst in this reaction zone comprises 3.0 percent by weight $WO_3$ and 5 weight percent by weight $MoO_3$ on a co-catalytic support comprising 60 percent by weight H-mordenite, large-pore crystalline aluminosilicate material suspended in a matrix of catalytically active alumina. Operating conditions in reaction zone 5 comprises a pressure of 300 psig, a temperature of about 850° F. to about 1000° F., a WHSV within the range of about 0.1 to about 20 weights of hydrocarbon per hour per weight of catalyst, and a hydrogen-to-hydrocarbon ratio that does not exceed 50,000 SCFB.

The effluent from reaction zone 5 is passed through line 7 to high pressure separator 8 wherein the light gases containing hydrogen are separated therefrom. The separated hydrogen-containing gas is passed through line 9 to line 3 to be recycled to reaction zone 5. Make-up hydrogen is added to this hydrogen-containing gas by way of line 10. The liquid effluent from high pressure separator 8 is passed through line 11 to control valve 12, which regulates the pressure of the reaction system and permits the pressure to be reduced prior to the passage of the liquid effluent through line 13 to fractionation zone 14. In fractionation zone 14, the liquid is separated into alkanes, which have resulted from some cracking occurring in the reaction zone, benzene, toluene, xylenes, and some trimethylbenzenes. Each of these streams is separated from one another in the fractionation zone. The alkanes are removed from fractionation zone 14 by way of line 15. Benzene is removed by way of line 16, while toluene is taken from line 17 and the xylene are removed by way of line 18. Small amounts of trimethylbenzenes are removed from fractionation zone 14 by way of line 19. Any residual hydrocarbons are removed by way of line 20.

The toluene in line 17 is conducted to line 2 where it joins the fresh feedstock from line 1 to be sent to reaction zone 5. Suitably, the xylene stream in line 18 may be sent to a second fractionation zone where the meta-xylene and para-xylene are separated from the ortho-xylene. The meta-xylene and para-xylene stream is passed to a fractional crystallization installation, where para-xylene is fractionally crystallized out of the meta-xylene. The para-xylene may be used in the manufacture of terephthalic acid, while the ortho-xylene may be passed to an isomerization reaction zone employing a catalyst similar to the catalyst that was used in the disproportionation reaction zone. However, in this reaction zone the meta-xylene is isomerized to an equilibrium mixture of xylenes. Any appreciable amounts of trimethylbenzenes be be separated by suitable means, such as fractional distillation, and the thusly-separated components can be re-cycled as feed or oxidized to appropriate organic acids, if this is desirable.

EXAMPLE II

Six catalysts were prepared as described hereinafter. These catalysts were identified as Catalysts A through F. The ability of each of these catalysts to disproportionate toluene was obtained by testing each as described in subsequent examples.

Catalyst A was prepared to contain 5.0 weight percent molybdenum oxide ($MoO_3$) and 3.0 weight percent tungsten oxide ($WO_3$) on a catalyst support comprising about 20 weight percent H-mordenite, large-pore crystalline aluminosilicate material suspended in a matrix of alumina (about 80 weight percent alumina).

A 68.2 gram portion of Zeolon-100H (Norton Chemical Co.) powder containing 12 (wgt) % water was slurried in 400 ml. of distilled water in a beaker which was held at ambient temperature.

A 2697 gram portion of PHF-alumina sol (American Cyanamid Corp.) containing 8.9 (wgt) % alumina ($Al_2O_3$) was thoroughly blended with the Zeolon-100H slurry with stirring using a Waring blender at a temperature of 25° C. The mixture was gelled by the addition of 400 ml of a 10% $NH_4OH$ solution at a temperature of 25° C. The gelled mixture was then dried at 120° C. for 20 hours in a drying oven, and then calcined at 540° C. (1000° F.) for 3 hours in flowing air. The resulting material consisting of 20 (wgt) % Zeolon-H and 80 (wgt) % alumina was ground to 20/40 mesh.

A portion of 92 grams of the above material was then impregnated with a 150 ml. aqueous solution containing 6.13 grams of ammonium hepta-molybdate $(NH_4)_6Mo_7O_2{}^2 \cdot 4H_2O$, and 3.26 grams of ammonium metatungstate, $(NH_4)_2W_4O_{13} \cdot 8H_2O$. The composite was dried in a drying oven at 120° C. for three hours, calcined in air for 3 hours at 540° C., and pelleted into $\frac{1}{4}'' \times \frac{1}{4}''$ pellets.

For both the drying and calcining steps, an air flow of about 1.5 cubic feet per hour was employed. About 4% Sterotex (Stokley-Van Camp) was used as a pelleting agent. Unless otherwise specified, the drying, pelleting and calcining of the subsequently-described catalysts were carried out under the above conditions. In each case, the calcined pellets were ground to provide a 20 to 40 mesh (U.S. Sieve) material.

Catalysts B through F were prepared as was Catalyst A but with varying compositions.

Catalyst G was prepared to comprise a copper-containing mordenite with an aluminum fluoride content. This catalyst is covered by Sato et al, U.S. Pat. No. 3,553,277, and is manufactured commercially by Tatoray-UOP. The catalyst was prepared to contain copper in an amount of 5 (wgt) % on a support of 80 (wgt) % of mordenite-H (Zeolon-100H) powder (Norton Chemical Co.) with 20 (wgt) % anhydrous $AlF_3$. The catalyst was made by blending 80 (wgt) % Zeolon-100H with 20 (wgt) % anhydrous $AlF_3$, forming into $\frac{1}{4}''$ pellets and calcining at 540° C. for 3 hours. A portion of 95 grams of the pellets was impregnated with copper solution containing 19 grams of cupric nitrate, $Cu(NO_3)_2 \cdot 3H_2O$, dried at 120° C. and calcined at 540° C. for 3 hours. The finished catalyst was ground to 20/40 mesh size for testing.

Catalyst H was a commercial catalyst for Ultracracking made by Davison Chemical Div., W. R. Grace Co. The catalyst was stated to contain 10 (wgt) % $MoO_3$ and 2.5 (wgt) % CoO supported on a high silica content silica-alumina matrix containing 35 (wgt) % Ultrastable (US) molecular sieve on 65 (wgt) % $SiO_2/Al_2O_3$. The catalyst, $\frac{1}{8}''$ pellets, was ground to 20/40 mesh size for testing. Catalyst I contained 5% $MoO_3$ and 3% $WO_3$ supported on a high silica content silica-alumina matrix containing 40 (wgt) % Ultrastable (US) molecular sieve on 60 (wgt) % Al$_2$O$_3$.

Compositions of the catalysts A through I were as follows:

| Catalyst | Composition |
|---|---|
| A | 5% MoO$_3$/3% WO$_3$/20% Mordenite-H, 80% Al$_2$O$_3$ |
| B | 5% MoO$_3$/3% WO$_3$/40% Mordenite-H, 60% Al$_2$O$_3$ |
| C | 5% MoO$_3$/3% WO$_3$/60% Mordenite-H, 40% Al$_2$O$_3$ |
| D | 5% MoO$_3$/3% WO$_3$/6% Mordenite-H, 94% Al$_2$O$_3$ |
| E | 5% MoO$_3$/0/6% Mordenite-H, 94% Al$_2$O$_3$ |
| F | 0/3% WO$_3$/6% Mordenite-H, 94% Al$_2$O$_3$ |
| G | 5% Cu/80% Mordenite-H, 20% AlF$_3$ |
| H | 10% MoO$_3$/2.5% CoO/(35% US-65% SiO$_2$/Al$_2$O$_3$) |
| I | 5% MoO$_3$/3% WO$_3$/(40% US-60% Al$_2$O$_3$) |

Each of the above catalysts was tested for its ability to disproportionate toluene. The feedstock that was employed in each of these tests was either a reagent grade toluene obtained from Baker and Adamson or essentially pure toluene obtained in barrel quantities from Demert and Dougherty Co.

The tests were performed in bench-scale test equipment which employed a reactor fabricated from a schedule-80 stainless steel pipe. This reactor was 20 inches long and had an I.D. of 0.622 inch. The reactor was heated externally by immersion in a constant-temperature salt bath. The temperature within the catalyst bed that was contained in the reactor was measured by means of a movable thermocouple in a coaxial thermowell which extended from the closure at the top of the reactor down through the vertical catalyst bed in the reactor. This thermowell had an O.D. of 0.125 inch. The resultant annular space within the reactor provided a space of 4.8 cc per inch of reactor length. Each catalyst was pulverized and screened into 20/40 mesh granules, that is, pass 20 mesh but not 40 mesh, prior to being charged to the lower section of the reactor. The catalyst loadings were varied between 4.0 and 8.0 grams of catalyst and occupied between 1 and 3 inches of reactor length. In some instances, catalyst was diluted with inert vycor chips to have a bed of about 5 inches. The space in the reactor above the catalyst bed was empty and served as a feed pre-heat section. The test unit was operated under once-through operation, i.e., the unit did not use recycled hydrocarbons and/or recycled hydrogen. Liquid and gaseous product streams were separated at the operating pressure. The liquid was collected in parallel high pressure receivers which were periodically isolated from the processing system and manually drained. When product samples were obtained for analytical purposes, they were collected in a small receiver during 1-hour periods at intervals of 24 hours and were analyzed by gas chromatographic methods. The bulk of the product, from overnight operation, was collected in a large receiver. The hydrogen-rich gas streams containing C$_1$-through C$_5$-hydrocarbons were analyzed by means of a gas chromatograph with a flame ionization detector and a 20'×⅛" column of OV-1 at room temperature. The liquid product was analyzed by a temperature-programmed dual column gas chromatograph with thermal conductivity detectors and 6'×¼" columns of SF-96.

Prior to introduction of the feed, the catalyst was treated with a hydrogen stream containing 8 volume percent hydrogen sulfide in order to sulfide the hydrogenation metals in the catalyst and to prevent the highly exothermic demethanation reaction from occurring. The pre-treatment was carried out at operating pressure with a gas flow rate of 3 SCFH for 2 hours. The temperature, initially 500° F., was raised to 750° F. during the first hour of the pre-treatment and was held at 750° F. for the second hour.

In general, each catalyst was tested for at least a one-day test. The operating conditions were: a pressure of 300 psig; a weight hourly space velocity (WHSV) of about 3.0 to about 13.3 grams of toluene per hour per gram of catalyst; a hydrogen rate of about 3,000 to 16,000 SCFB; and a catalyst temperature of about 700° F. to about 960° F. The unit was operated to achieve about 35 weight percent conversion of the toluene with the once-through operation.

The results of testing the several types of catalysts are shown in Table I. Activity of Catalyst A is shown as typical of the composition of catalysts of the invention.

TABLE I

Catalyst Composition vs. Disproportionation Activity

| Feed: Test Conditions | | Toluene |
|---|---|---|
| Reactor pressure: | | 300 psig |
| Reactor Temperature: | | 900° F. |
| H$_2$/Toluene Mole Ratio: | | 9.2:1 |
| WHSV (Wgt of Feed/Hr/Wgt of Catalyst): | | 6.0 |
| Hours on Stream: | | 44 |

| | Composition | | Disproportionation Activity (Conversion to Benzene and Xylenes) |
|---|---|---|---|
| Catalyst | Metals | Support | Wgt. % of Feed |
| A | 5% MoO$_3$ 3% WO$_3$ | 20% Mordenite-H 80% Al$_2$O$_3$ | 40.7 |
| G | 5% Cu | 80% Mordenite-H 20% AlF$_3$ | 33.0 |
| H | 10% MoO$_3$ 2.5% CoO | 35% U.S. Sieve 65% silica-alumina | 30.7 |
| I | 5% MoO$_3$ 3% WO$_3$ | 40% U.S. Sieve 60% Al$_2$O$_3$ | 29.4 |

While the above results indicate that the invented catalyst is suitable for disproportionation of alkylaromatic hydrocarbons, and is superior to others containing either different support materials or different metals, correlation presented in the following examples provide an insight into what the preferred catalytic composition should be for the disproportionation process that is disclosed herein. In these examples, various combinations of selected portions of the data obtained with the above-described catalysts are studied to show the effect of the concentration of aluminosilicate material, the effect of the type of aluminosilicate material, the effect of the type of hydrogenation component, and the effect of the type of matrix material in the support upon catalyst performance for the disproportionation of toluene.

EXAMPLE III

The data presented in this example, Example III, indicate that, as the concentration of the aluminosilicate material is increased, the relative catalyst activity is increased and, the relative activity for disproportionating toluene is increased.

It indicates that the preferred catalyst support comprises a composite of the large-pore crystalline aluminosilicate material, a refractory inorganic oxide, and selected percentages of the oxides of at least two Group VIb metals.

The catalysts, which were prepared and tested as described hereinabove in Example II, were Catalysts A, B, C, and D.

Each of these catalysts comprised its respective hydrogenation component deposited upon a catalyst support comprising 6 to 60 weight percent mordenite-H, large-pore crystalline aluminosilicate material suspended in and distributed throughout a matrix of alumina.

The data obtained from this example are presented in Table II, in which activity has been expressed as the disproportionation rate constant calculated for a temperature of 900° F.

The results obtained in this example indicate that the catalyst having the 60% mordenite-H, 40% Al$_2$O$_3$ component i.e., Catalyst C, provided the best conversion to benzene and xylenes and highest relative activity.

As a measure of catalyst performance, an activity number can be calculated from the data as to the operating conditions and the conversion rates to the desired products based upon an empirical reaction rate constant.

Activity is correlated to the weight hourly space velocity (WHSV) so that catalyst loading and feed rate to attain a given conversion can be conveniently calculated from the activity relationship. The rate of toluene disproportionation is expressed in terms of a dimensionless concentration "Z" defined as "a fractional departure from equilibrium". The assumed reaction order is 1.5. The empirical formula of the rate constant, K$_D$, is accordingly $$\frac{K_D}{WHSV} = 2\left(\frac{1}{\sqrt{Z}} - 1\right)$$

wherein $$Z = \frac{K - x/(1 - S)}{K - X_o/(1 - S_o)}$$

and where X and S are weight fractions of aromatic products (benzene, xylenes and C$_9$+ aromatics) and saturates respectively. X$_o$ S$_o$ denote the corresponding impurities in the toluene feed. Equilibrium toluene conversion which is 59 (wgt) % at 800° F. and 59.3 (wgt) % at 900° F. is represented over the temperature range of 750°–950° F. by the formula K=0.59 [Exp. 80.1×{1/1260−1/(460+°F.)}]

The activity number for toluene disproportionation, D$_A$, is defined by referring to the reaction rate constant, K$_D$, at 900° F. and multiplying an arbitrary factor of 10 as follows:

$$D_A = (WHSV)\, 20\left(\frac{1}{\sqrt{Z}} - 1\right) \cdot Exp.\left\{\frac{21}{1.987}\left(\frac{1800}{460 + °F.} - \frac{1800}{1360}\right)\right\}$$

The activation energy for the toluene disproportionation reaction used was 21 Kcal/mole.

TABLE II

Effect of H-Mordenite Content on Activity

| Feed: Test Conditions: | Toluene |
|---|---|
| Reactor Pressure | 300 psig |
| H$_2$/Toluene Mole Ratios | 9.2:1 |
| Hours On Stream | 44 |

| Catalyst | Composition Metals | Composition Support | Reaction Temp °F. | WHSV | Conversion to Benzene & Xylenes Wgt. % of Feed | Catalyst Activity Number |
|---|---|---|---|---|---|---|
| D | 5% MoO$_3$ 3% WO$_3$ | 6% Mordenite-H 94% Al$_2$O$_3$ | 900 | 6.0 | 32.1 | 66 |
| A | 5% MoO$_3$ 3% WO$_3$ | 20% Mordenite-H 80% Al$_2$O$_3$ | 900 | 6.0 | 40.7 | 132 |
| B | 5% MoO$_3$ 3% WO$_3$ | 40% Mordenite-H 60% Al$_2$O$_3$ | 900 | 12.5 | 37.0 | 207 |
| C | 5% MoO$_3$ 3% WO$_3$ | 60% Mordenite-H 40% Al$_2$O$_3$ | 800 | 13.3 | 36.7 | 560 |

Because of very high catalytic activity, Catalyts B and C had to be tested at less severe conditions, i.e., a higher space velocity (WHSV) or at a lower temperature. These differences in test conditions were accounted for by use of an activity number.

The activity number represents an empirical measure of catalyst performance and is calculated from the conversion to the desired products and operating conditions.

EXAMPLE IV

The data presented in this example, Example IV, indicate the presence of a Group VIb metal, molybdenum, with Group VIb metal tungsten, and mordenite and alumina provides a more active catalyst than those containing only a single Group VIb metal.

In this example, the data obtained from a select member of the catalysts that were prepared and tested as described hereinabove in Example II were compared to show the effect of the metals content upon conversion of toluene to benzene and xylenes, as well as the effect upon activity. The catalysts that were employed in this example were Catalysts D, E, and F. Each of these catalysts comprised a hydrogenation component and large-pore crystalline aluminosilicate material. The results of this study are summarized in Table III.

TABLE III

Effect of Metals Content Upon Conversion

| Feed: Test Conditions | Toluene |
|---|---|
| Pressure: | 300 psig |

TABLE III-continued

| Temperature: | 900° F. |
|---|---|
| H₂/Toluene Mole Ratio: | 9.2:1 |
| WHSV: | 6.0 |
| Hours on Stream: | 20 |

| | | Composition | | |
|---|---|---|---|---|
| | Metals | Support | Disproportionation Activity (Conversion to Benzene and Xylenes) Wgt. % Feed | Activity Number |
| D | 5% MoO$_3$ 3% WO$_3$ | 6% Mordenite-H 94% Al$_2$O$_3$ | 34.0 | 76.4 |
| E | 5% MoO$_3$ | 6% Mordenite-H 94% Al$_2$O$_3$ | 29.8 | 58.4 |
| F | 3% WO$_3$ | 6% Mordenite-H 94% Al$_2$O$_3$ | 19.8 | 28.5 86.9 |

EXAMPLE V

The performance of a number of catalysts having supports comprising different amounts of mordenite large-pore crystalline aluminosilicate material were compared in this example. These catalysts, which were prepared and tested as described in Example II, were Catalysts A, B, C, and D.

Each of the catalysts A, B, C and D had a hydrogenation component comprising the oxides of tungsten and molybdenum. The supports of these catalysts comprised 6-60 weight percent aluminosilicate material mordenite-H suspended in and distributed throughout a matrix of high-alumina silica-alumina.

The results of Example V demonstrate that catalysts which have multi-component supports comprising aluminosilicate material and alumina in certain percentages are of increasing activity. Moreover, the activities exhibited by these catalysts are better to an extent wherein the equivalent disproportionation temperature (EDT) is substantially less as the amount of aluminosilicate material increases. The results are in Table IV.

TABLE IV
Activity of the Invented Catalysts

| Catalyst | D | A | B | C |
|---|---|---|---|---|
| Metals: 5% MoO$_3$-3WO$_3$ | | | | |
| Mordenite-H, % | 6 | 20 | 40 | 60 |
| Run hours | 44 | 43 | 43 | 43 |
| Run Conditions | | | | |
| PSIG | 300 | 300 | 300 | 300 |
| H$_2$, MSCF/B | 14.7 | 15.4 | 15.0 | 13.7 |
| °F. | 902 | 898 | 905 | 803 |
| WHSV | 5.98 | 5.95 | 12.49 | 13.28 |
| Wgt % Yields | | | | |
| Disproportionates | 34.43 | 44.29 | 40.29 | 40.56 |
| Saturates | 2.35 | 3.29 | 2.55 | 2.66 |
| Activity, D$_A$ | 65.8 | 132 | 207 | 618 |
| EDT, °F. | 913 | 848 | 808 | 724 |

EDT: Equivalent disproportionation temperature at the conditions to yield 36.20 wgt % products of Control Run.

EXAMPLE VI

The performance of seven catalysts were compared to demonstrate the effect of hydrogenation components and the concentration of mordenite aluminosilicate material upon catalyst deactivation. These seven catalyts, which were prepared and tested as described in Example II, were Catalysts A, B, C, D, E, F, and K. These catalysts were prepared with catalyst supports of mordenite-H (Zeolon-H), large-pore crystalline aluminosilicate material of 6, 20, 40 and 60 (wgt)% in a refractory inorganic oxide. Catalysts A, B, C and D contained hydrogenation components comprising 3 weight percent tungsten oxide and 5 weight percent molybdenum trioxide, based upon the weight of the catalyst. Catalyst E contained 5 (wgt)% MoO$_3$ upon a catalyst support comprising 6 (wgt)% mordenite-H, large-pore crystalline aluminosilicate material in a refractory inorganic oxide. Catalyst F contained 3 (wgt)% WO$_3$ upon a catalyst support comprising 6 (wgt)% mordenite-H, large-pore crystalline aluminosilicate material in a refractory inorganic oxide. Catalyst K contained a hydrogenation component comprising 6 wgt% tungsten oxide with a catalyst support of 80 wgt% of mordenite-H and 20 wgt% refractory inorganic oxide. The data obtained from the study described in this example are presented in Table V, wherein activity is expressed as the disproportionation rate constant calculated for a temperature of 900° F.

These results confirm the data of the previous examples that the oxides of tungsten and molybdenum constitute a preferred hydrogenation component and that a support comprising mordenite-H, large-pore crystalline aluminosilicate material and a refractory inorganic oxide is a preferred catalyst support for the catalysts of the process of the present invention.

TABLE V
Effect of Hydrogenation Components and Concentration of Mordenite-H

| | Composition - % | | | | | |
|---|---|---|---|---|---|---|
| Catalyst | MoO$_3$ | WO$_3$ | Mordenite-H as % of Base | Run Hrs | Catalyst Activity Number D$_A$ | Selectivity K$_S$ | Saturate Yield Wgt. % |
| A | 5 | 3 | 20 | 43 | 133 | — | 3.6 |
| B | 5 | 3 | 40 | 43 | 129 | 5.28 | 2.6 |
| C | 5 | 3 | 60 | 45 | 423 | 5.22 | 3.2 |
| D | 5 | 3 | 6 | 44 | 65.8 | 6.06 | 2.4 |
| E | 5 | 0 | 6 | 44 | 54.8 | 6.07 | 2.1 |
| F | 0 | 3 | 6 | 24 | 28.5 | 2.97 | 0.7 |
| K | 0 | 6 | 80 | 44 | 199 | 4.73 | 2.5 |

EXAMPLE VII

The performances of four catalysts were compared to demonstrate the effect of both hydrogenation components and the concentration of aluminosilicate material upon catalyst deactivation. These four catalysts which were prepared and tested as described in Example II were Catalysts B, D, G and H. Catalysts B and D were prepared with catalyst supports comprising 5 weight percent of molybdenum trioxide, 3 weight percent of tungsten trioxide, and 6 and 40 weight percent mordenite-H as a percentage of the base catalyst support suspended in and distributed throughout a matrix of alumina. Catalyst H contained hydrogenation components comprising 10 weight percent molybdenum trioxide and 2.5 weight percent cobalt oxide, based upon the weight of the catalyst with catalyst support comprising about 35 weight percent ultrastable large-pore crystalline aluminosilicate material suspended in and distributed throughout a matrix of silica-alumina. Catalyst G contained as a hydrogenation component 5 weight percent copper with a catalyst support comprising 80 weight percent mordenite-H with 20 weight percent anhydrous aluminum fluoride, based on the weight of the catalyst. The data obtained from the study described in this are summarized in Table VI and presented diagrammatically in FIG. 2, wherein activity maintenance is expressed as the disproportionation rate constant relative to the initial value for each respective catalyst.

Figure 2:
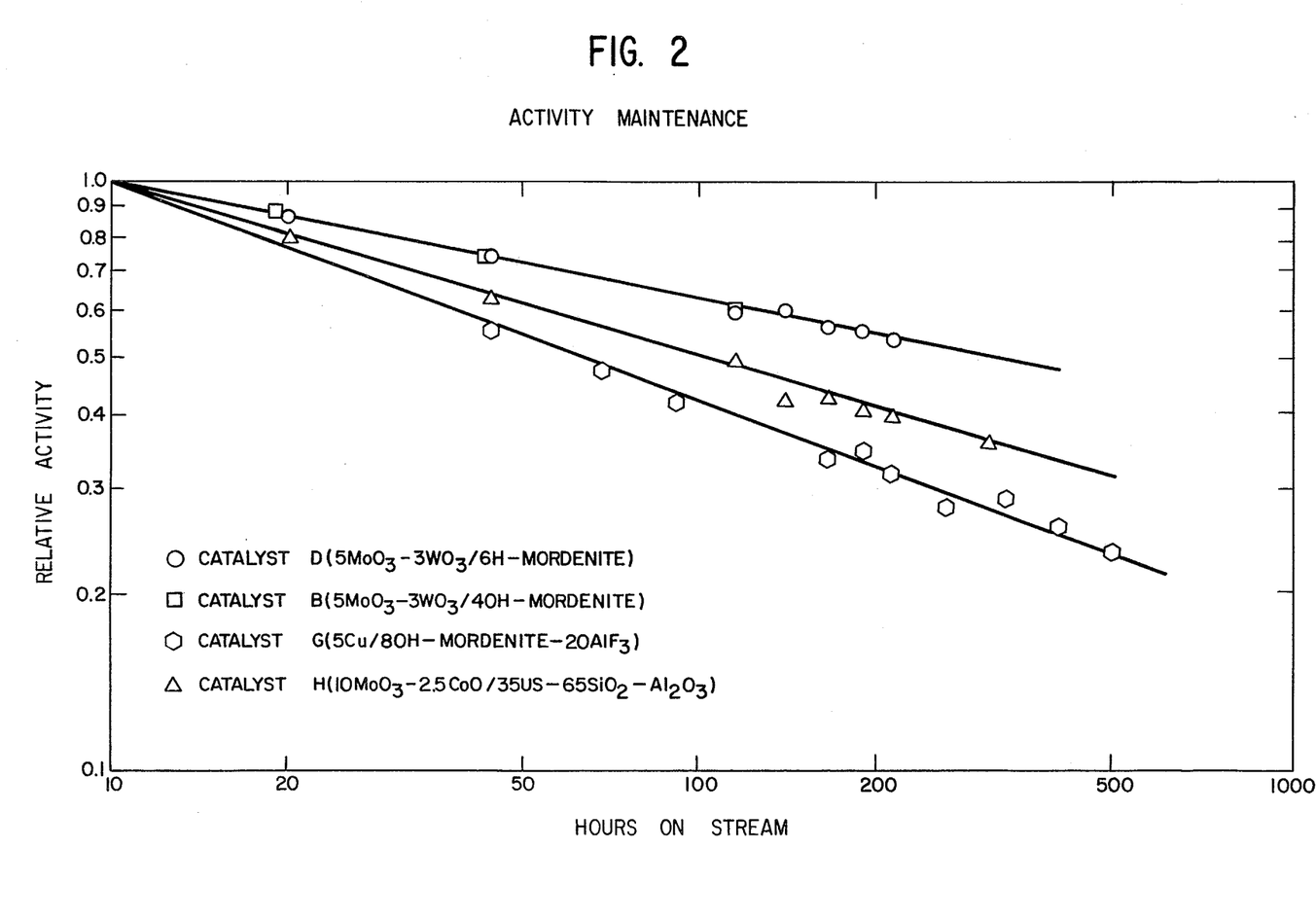
FIG. 2 exhibits the effect of hydrogenation components and the concentration of aluminosilicate material on catalyst deactivation for the disproportionation of toluene.

The data in FIG. 2 demonstrate that the oxides of molybdenum and tungsten on mordenite-alumina of the present invention provide a slower rate of deactivation. Furthermore, the data in Table VI show that the catalysts having a hydrogenation component comprising the oxides of molybdenum and tungsten and a co-catalytic support of mordenite-H upon a matrix of alumina are more active than the other catalysts which employ either oxides of molybdenum and cobalt upon a support of ultrastable, large pore crystalline aluminosilicate material upon a matrix of silica-alumina, or copper upon a support of mordenite-H with anhydrous aluminum fluoride.

Because of the high catalytic activity of Catalyst B, the data on Catalyst B had to be obtained at less severe conditions, i.e., a higher space velocity (WHSV). In contrast, the data on Catalyst G at 332 hours, because of lower activity, had to be obtained at a lower space velocity of 3.4 WHSV. The other conditions were: $H_2$ in thousand std cubic feet/barrel (MSCFB) ranged from 13.3 to 18.1; temperature was $900° \pm 6°$ F.

These results confirm the data of the previous examples that the oxides of molybdenum and tungsten constitute a preferred hydrogenation component and that a support comprising a mordenite-type large pore crystalline aluminosilicate material and a refractory inorganic oxide is a preferred catalyst support for the catalysts of the process of the present invention.

mordenite large pore crystalline aluminosilicate material and a refractory inorganic oxide consisting essentially of a catalytically active alumina selected from the group consisting of gamma-alumina and eta-alumina, wherein said mordenite large pore crystalline aluminosilicate material of said acidic cracking component is suspended in and dispersed throughout a matrix of said inorganic oxide.

2. The composition of claim 1 wherein the said tungsten/molybdenum component comprises tungsten in an amount within the range of about 1 weight percent to about 10 weight percent, expressed as $WO_3$ and based upon the total weight of said catalytic composition, and molybdenum in an amount within the range of about 1 weight percent to about 20 weight percent expressed as $MoO_3$ and based upon the total weight of said catalytic composition.

3. The composition of claim 1 wherein said mordenite, large-pore crystalline aluminosilicate material is present in said acidic cracking component in an amount within the range of about 5 weight percent to about 95 weight percent based upon the weight of said cracking component, said mordenite being characterized by a theoretical silica-to-alumina ratio that is about 10 to 1, the effective pore diameter in Angstroms (Å) is within the range of 6 to 9 Å, and the surface area in square meters/gram is within the range of 400–450 $m^2/g$.

4. The composition of claim 1 wherein said catalytically active alumina is present in said acidic cracking component in an amount within the range of about 5

TABLE VI

Effect of Hydrogenation Components And Concentration of Aluminosilicate Material Upon Catalyst Deactivation

| Catalyst | Composition | Hrs On Stream | WHSV | Total Aromatics Wgt. % of Feed | Activity Number | Activity Relative to Initial Activity@ 10 Hrs. |
|---|---|---|---|---|---|---|
| B | 5MoO$_3$/3WO$_3$/40Mordenite-H | 19 | 12.5 | 43.8 | 247 | 0.89 |
|   |   | 43 | 12.5 | 40.6 | 207 | 0.75 |
|   |   | 115 | 12.5 | 37.9 | 167 | 0.61 |
| D | 5 MoO$_3$/3WO$_3$/6Mordenite-H | 20 | 6.0 | 36.8 | 76.4 | 0.87 |
|   |   | 44 | 6.0 | 34.4 | 65.8 | 0.75 |
|   |   | 116 | 6.0 | 30.5 | 52.7 | 0.60 |
|   |   | 140 | 6.0 | 31.1 | 53.7 | 0.61 |
|   |   | 164 | 6.0 | 29.9 | 50.0 | 0.57 |
|   |   | 188 | 6.0 | 29.5 | 49.4 | 0.56 |
|   |   | 212 | 6.0 | 28.9 | 47.7 | 0.54 |
| G | 5 Cu/80Mordenite-H/20 AlF$_3$ | 20 | 6.0 | 43.3 | 114.0 | 0.88 |
|   |   | 44 | 6.0 | 36.2 | 72.1 | 0.56 |
|   |   | 68 | 6.0 | 33.6 | 61.7 | 0.48 |
|   |   | 92 | 6.0 | 31.3 | 53.8 | 0.42 |
|   |   | 164 | 6.0 | 27.5 | 43.5 | 0.34 |
|   |   | 188 | 6.0 | 28.1 | 45.3 | 0.35 |
|   |   | 212 | 6.0 | 26.6 | 41.0 | 0.32 |
|   |   | 332 | 3.4 | 34.9 | 38.2 | 0.29 |
|   |   | 404 | 3.4 | 33.0 | 34.1 | 0.26 |
|   |   | 500 | 3.4 | 30.9 | 30.5 | 0.24 |
| H | 10 MoO$_3$/2.5 CoO/35 US - 65 SiO$_2$/Al$_2$O$_3$ | 20 | 6.0 | 36.4 | 83.1 | 0.81 |
|   |   | 44 | 6.0 | 32.8 | 65.7 | 0.64 |
|   |   | 116 | 6.0 | 28.0 | 51.0 | 0.50 |
|   |   | 140 | 6.0 | 25.8 | 43.8 | 0.43 |
|   |   | 164 | 6.0 | 26.9 | 43.6 | 0.43 |
|   |   | 188 | 6.0 | 26.2 | 42.2 | 0.41 |
|   |   | 212 | 6.0 | 25.5 | 40.4 | 0.40 |
|   |   | 308 | 6.0 | 24.2 | 36.9 | 0.36 |

What is claimed is:

1. A catalytic composition for disproportionation of petroleum hydrocarbons consisting essentially of a tungsten/molybdenum component deposited upon an acidic cracking component consisting essentially of a weight percent to about 95 weight percent based upon the weight of said cracking component, said catalytically active alumina being selected from the group consisting of gamma-alumina and eta-alumina with a pore diameter of about 70 Angstroms (Å) to about 200 Å and a surface area within the range of from about 200 square meters per gram to about 500 square meters per gram.

5. The composition of claim 1 wherein said catalytic composition comprises a tungsten/molybdenum component of 3 weight percent $WO_3$ and 5 weight percent $MoO_3$ of total weight of said catalytic composition and an acidic cracking component comprising 60 weight percent mordenite and 40 weight percent catalytically active alumina of total weight of said acidic cracking component.

6. The composition of claim 5 wherein said mordenite is mordenite-H.

7. The composition of claim 5 wherein said catalytically active alumina is gamma-alumina.

* * * * *

UNITED STATES PATENT OFFICE
CERTIFICATE OF CORRECTION

Patent No. 4,330,435    Dated May 18, 1982

Inventor(s) Ralph J. Bertolacini, Dae K. Kim and G.M. Lehmann

It is certified that error appears in the above-identified patent and that said Letters Patent are hereby corrected as shown below:

Patent Reads

| Col | Line  | |
|-----|-------|--|
| 12  | 21-22 | TABLE I |

Feed:
  Test Conditions        Toluene

TABLE I should read:

Feed:                  Toluene
  Test Conditions

| 14 | 19-20 | TABLE II |

Feed:
  Test Conditions        Toluene

TABLE II should read:

Feed:                  Toluene
  Test Conditions

UNITED STATES PATENT OFFICE
CERTIFICATE OF CORRECTION

Patent No. 4,330,435  Dated May 18, 1982

Inventor(s) Ralph J. Bertolacini et al.

It is certified that error appears in the above-identified patent and that said Letters Patent are hereby corrected as shown below:

Patent Reads
Col.  Line 15    16-17    TABLE III

F  3%$WO_3$    6% Mordenite-H    19.8    28.5
               94% $Al_2O_3$              86.9

TABLE III should read

F  3%$WO_3$    6% Mordenite-H    19.8    28.5
               94% $Al_2O_3$

Signed and Sealed this

Ninth Day of November 1982

[SEAL]

Attest:

GERALD J. MOSSINGHOFF

Attesting Officer   Commissioner of Patents and Trademarks